United States Patent
Ognibene et al.

(10) Patent No.: US 9,645,077 B2
(45) Date of Patent: May 9, 2017

(54) SPECTROSCOPIC QUANTIFICATION OF EXTREMELY RARE MOLECULAR SPECIES IN THE PRESENCE OF INTERFERING OPTICAL ABSORPTION

(71) Applicants: Lawrence Livermore National Security, LLC, Livermore, CA (US); Picarro, Inc., Santa Clara, CA (US)

(72) Inventors: Ted Ognibene, Oakland, CA (US); Graham Bench, Livermore, CA (US); Alan Daniel McCartt, San Francisco, CA (US); Kenneth Turteltaub, Livermore, CA (US); Chris W. Rella, Sunnyvale, CA (US); Sze Tan, Sunnyvale, CA (US); John A. Hoffnagle, San Jose, CA (US); Nabil Saad, Menlo Park, CA (US); Eric Crosson, Livermore, CA (US)

(73) Assignees: Lawrence Livermore National Security, LLC, Livermore, CA (US); Picarro, Inc., Santa Clara, CA (US)

( * ) Notice: Subject to any disclaimer, the term of this patent is extended or adjusted under 35 U.S.C. 154(b) by 0 days.

(21) Appl. No.: 14/714,658

(22) Filed: May 18, 2015

(65) Prior Publication Data
US 2016/0011101 A1    Jan. 14, 2016

Related U.S. Application Data

(60) Provisional application No. 62/024,088, filed on Jul. 14, 2014.

(51) Int. Cl.
*G01N 21/00* (2006.01)
*G01N 21/31* (2006.01)
(Continued)

(52) U.S. Cl.
CPC .......... *G01N 21/3103* (2013.01); *G01J 3/027* (2013.01); *G01J 3/28* (2013.01);
(Continued)

(58) Field of Classification Search
CPC .... G01J 3/42; G01J 3/027; G01J 3/28; G01N 21/3103; G01N 2021/391;
(Continued)

(56) References Cited

U.S. PATENT DOCUMENTS 6,466,322 B1    10/2002    Paldus et al.
7,106,763 B2     9/2006    Tan et al.
(Continued)

OTHER PUBLICATIONS

Friedrichs et al., "Toward Continuous Monitoring of Seawater 13C02/12C02 Isotope Ratio and pC02: Performance of Cavity Ringdown Spectroscopy and Gas Matrix Effects," Limnology and Oceanography: Methods, vol. 8, No. 1, 2010, pp. 539-551.
(Continued)

*Primary Examiner* — Tri T Ton
(74) *Attorney, Agent, or Firm* — Eddie E. Scott

(57) ABSTRACT

Optical spectrometer apparatus, systems, and methods for analysis of carbon-14 including a resonant optical cavity configured to accept a sample gas including carbon-14, an optical source configured to deliver optical radiation to the resonant optical cavity, an optical detector configured to detect optical radiation emitted from the resonant cavity and to provide a detector signal; and a processor configured to compute a carbon-14 concentration from the detector signal, wherein computing the carbon-14 concentration from the detector signal includes fitting a spectroscopic model to a measured spectrogram, wherein the spectroscopic model accounts for contributions from one or more interfering species that spectroscopically interfere with carbon-14.

18 Claims, 6 Drawing Sheets

(51) Int. Cl.

| | |
|---|---|
| *G01J 3/42* | (2006.01) |
| *H01J 49/00* | (2006.01) |
| *G01N 21/39* | (2006.01) |
| *G01J 3/28* | (2006.01) |
| *G01J 3/02* | (2006.01) |

(52) U.S. Cl.
CPC ............... *G01J 3/42* (2013.01); *G01N 21/39* (2013.01); *H01J 49/0086* (2013.01); *G01N 2021/391* (2013.01); *G01N 2021/399* (2013.01)

(58) Field of Classification Search
CPC ............ G01N 2021/399; G01N 21/39; G01N 2201/0612; H01J 49/0086; H01J 49/0495; H04N 1/00496
USPC .................................................. 356/432–442
See application file for complete search history.

(56) References Cited

U.S. PATENT DOCUMENTS

| 7,154,595 | B2 | 12/2006 | Paldus et al. |
|---|---|---|---|
| 8,264,688 | B1 | 9/2012 | Tan |
| 8,325,343 | B2 | 12/2012 | Cole et al. |
| 8,537,362 | B2 | 9/2013 | He et al. |
| 2008/0086038 | A1* | 4/2008 | Thornton ........... A61B 5/14532 600/310 |
| 2008/0111993 | A1 | 5/2008 | Miller |
| 2012/0241622 | A1 | 9/2012 | Heyne et al. |
| 2013/0066224 | A1 | 3/2013 | Assadi-Porter et al. |

OTHER PUBLICATIONS

International Search Report and Written Opinion for PCT/US15/036927, corresponding to U.S. Appl. No. 14/714,658, 19 pages.
Cancio et al. "Saturated-Absorption Cavity Ring-Down (SCAR) for High-Sensitivity and High-Resolution Molecular Spectroscopy in the Mid IR," G. Gagliardi, H.-P. Loock (eds.), Cavity-Enhanced Spectroscopy and Sensing,, Springer Series in Optical Sciences 179, Ch. 4, 2014, pp. 143-162.
Crosson, "A Cavity Ring-Down Analyzer for Measuring Atmospheric Levels of Methane, Carbon Dioxide, and Water Vapor," Appl. Phys. B, 92, 2008, pp. 403-408.
Galli et al., "Molecular Gas Sensing Below Parts Per Trillion: Radiocarbon-Dioxide Optical Detection," Phys. Ref. Lett. 107, 2011, pp. 270802-1-270802-4.
Giusfredi et al., "Saturated-Absorption Cavity Ring-Down Spectroscopy," Phys. Rev. Lett. 104, 2010, pp. 110801-1-110804-4.
Labrie et al., "Radiocarbon Dating by Infrared Laser Spectroscopy," Appl. Phys., vol. 24, 1981, pp. 381-386.
McCartt, "Development of a Low-Temperature Cavity Ring-Down Spectrometer for the Detection of Carbon-14," Dissertation submitted to the Dept. of Mech. Eng. at Stanford University, 2014, 173 pages.
Ognibene et al., "A New Accelerator Mass Spectrometry System for 14C-Quanitification of Biochemical Samples", Int'l J. of Mass Spec., vol. 218, 2002, pp. 255-265.
Rothman et al., "The HITRAN2012 Molecular Spectroscopic Database," J. Quant. Spectrosc. Radiat. Transfer 130, 2013, pp. 4-50.
Stowasser et al., "A Low-Volume Cavity Ring-Down Spectrometer for Sample-Limited Applications," Appl. Phys. B, vol. 116, 2014, pp. 1-16.
The Center for Accelerator Mass Spectrometry, Science & Technology Rev., 1997, 4 pp.
Zalicki et al., "Cavity Ring-Down Spectroscopy for Quantitative Absorption Measurements," J. Chem. Phys., vol. 102, 1995, pp. 2708-2717.

* cited by examiner

US 9,645,077 B2

SPECTROSCOPIC QUANTIFICATION OF EXTREMELY RARE MOLECULAR SPECIES IN THE PRESENCE OF INTERFERING OPTICAL ABSORPTION

CROSS-REFERENCE TO RELATED APPLICATIONS

This application claims priority to and benefit under 35 U.S.C. §119(e) of U.S. Provisional Patent Application No. 62/024,088 filed Jul. 14, 2014 entitled "measuring 14C in biochemical samples using optical spectroscopy," the content of which is hereby incorporated by reference in its entirety for all purposes.

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to spectroscopy and more particularly to cavity ring down spectroscopy.

State of Technology

This section provides background information related to the present disclosure which is not necessarily prior art.

Biological AMS is a technique in which carbon-14 is used as a tag to study, with extreme precision and sensitivity, complex biological processes, such as cancer, molecular damage, drug and toxin behavior, nutrition and other areas. When biological accelerator mass spectrometry (AMS) was first developed the process of preparing the samples was time-consuming and cumbersome. Physicists and biomedical researchers used torches, vacuum lines, special chemistries and high degrees of skill to convert biological samples into graphite targets that could then be run through the AMS system. At that time, it took two days of work to prepare only eight samples. Additional information about Accelerator Mass Spectrometry is contained in the article: "A New World of Biomedical Research: The Center for Accelerator Mass Spectrometry," Science & Technology Review, November 1997, pp. 6-11, a portion of which is reproduced below.

Mass spectrometry has been used since early in this century to study the chemical makeup of substances. A sample of a substance is put into a mass spectrometer, which ionizes it and looks at the motion of the ions in an electromagnetic field to sort them by their mass-to-charge ratios. The basic principle is that isotopes of different masses move differently in a given electromagnetic field.

An accelerator was first used as a mass spectrometer in 1939 by Luis Alvarez and Robert Cornog of the University of California at Berkeley. To answer what at the time was a knotty nuclear physics question, they used a cyclotron to demonstrate that helium-3 was stable and was not hydrogen-3 (tritium), which is not stable. Accelerators continued to be used for nuclear physics, but it was not until the mid-1970s that they began to be used for mass spectrometry. The impetus then was to improve and expand radiocarbon dating. Van de Graaff accelerators were used to count carbon-14 ($^{14}C$) for archaeologic and geologic dating studies.

Accelerator mass spectrometry (AMS) quickly became the preferred method for radiocarbon dating because it was so much quicker than the traditional method of scintillation counting, which counts the number of $^{14}C$ atoms that decay over time. The half-life of $^{14}C$ is short enough (5,730 years) that counting decayed atoms is feasible, but it is time-consuming and requires a relatively large sample. Other radioactive isotopes have half-lives as long as 16 million years and thus have such slow decay rates that huge samples and impossibly long counting times are required. The high sensitivity of AMS meant that these rare isotopes could be measured for the first time.

Before a sample ever reaches the AMS unit, it must be reduced to a solid form that is thermally and electrically conductive. All samples are carefully prepared to avoid contamination. They are reduced to a homogeneous state from which the final sample material is prepared. Carbon samples, for instance, are reduced to graphite. Usually just a milligram of material is needed for analysis. If the sample is too small, bulking agents are carefully measured and added to the sample.

The article: "A New World of Biomedical Research: The Center for Accelerator Mass Spectrometry," Science & Technology Review, November 1997, pp. 6-11, is incorporated herein in its entirety by this reference.

Additional information about accelerator mass spectrometry is contained in the article: "A New Accelerator Mass Spectrometry System for $^{14}C$ quantification of Biochemical Samples," by Ted J. Ognibene, Graham Bench, Tom A. Brown, Graham F. Peaslee, and John S. Vogel, in International Journal of Mass Spectrometry 218 (2002) 255-264, a portion of which is reproduced below.

Accelerator mass spectrometry (AMS) provides carbon isotope ratio quantification at part per quadrillion sensitivity in milligram-sized samples with part per thousand precision. AMS was originally developed for use in the geosciences and archeology as a means to determine radiocarbon ages. AMS has been used in the biosciences to provide highly sensitive $^{14}C$ quantification at environmentally relevant doses. Recent conference proceedings highlight experiments using $^{14}C$, as well as other isotopes of biological significance. However, $^{14}C$ remains one of the most widely used tracers in biochemical studies of toxicology, nutrition, carcinogenesis, pharmacokinetics and protein quantification.

The article: "A New Accelerator Mass Spectrometry System for $^{14}C$-quantification of Biochemical Samples," by Ted J. Ognibene, Graham Bench, Tom A. Brown, Graham F. Peaslee, and John S. Vogel, in International Journal of Mass Spectrometry 218 (2002) 255-264, is incorporated herein in its entirety by this reference.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

The inventors have developed apparatus, systems, and methods to quantify the amount of $^{14}C$ derived from biochemicals using cavity ring down spectroscopy (CRDS). The inventor's apparatus, systems, and methods provide an optical spectrometer for analysis of carbon-14 including a resonant optical cavity configured to accept a sample gas including carbon-14, an optical source configured to deliver optical radiation to the resonant optical cavity, an optical detector configured to detect optical radiation emitted from the resonant cavity and to provide a detector signal; and a processor configured to compute a carbon-14 concentration from the detector signal, wherein computing the carbon-14 concentration from the detector signal includes fitting a spectroscopic model to a measured spectrogram, wherein the spectroscopic model accounts for contributions from one or more interfering species that spectroscopically interfere with carbon-14.

The inventor's apparatus, systems, and methods can be used for the measurement of trace gases. The inventor's apparatus, systems, and methods have the potential for replacing liquid Scintillation Counting, as well as Accelerator Mass Spectrometry (in certain instances).

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Figure 1:
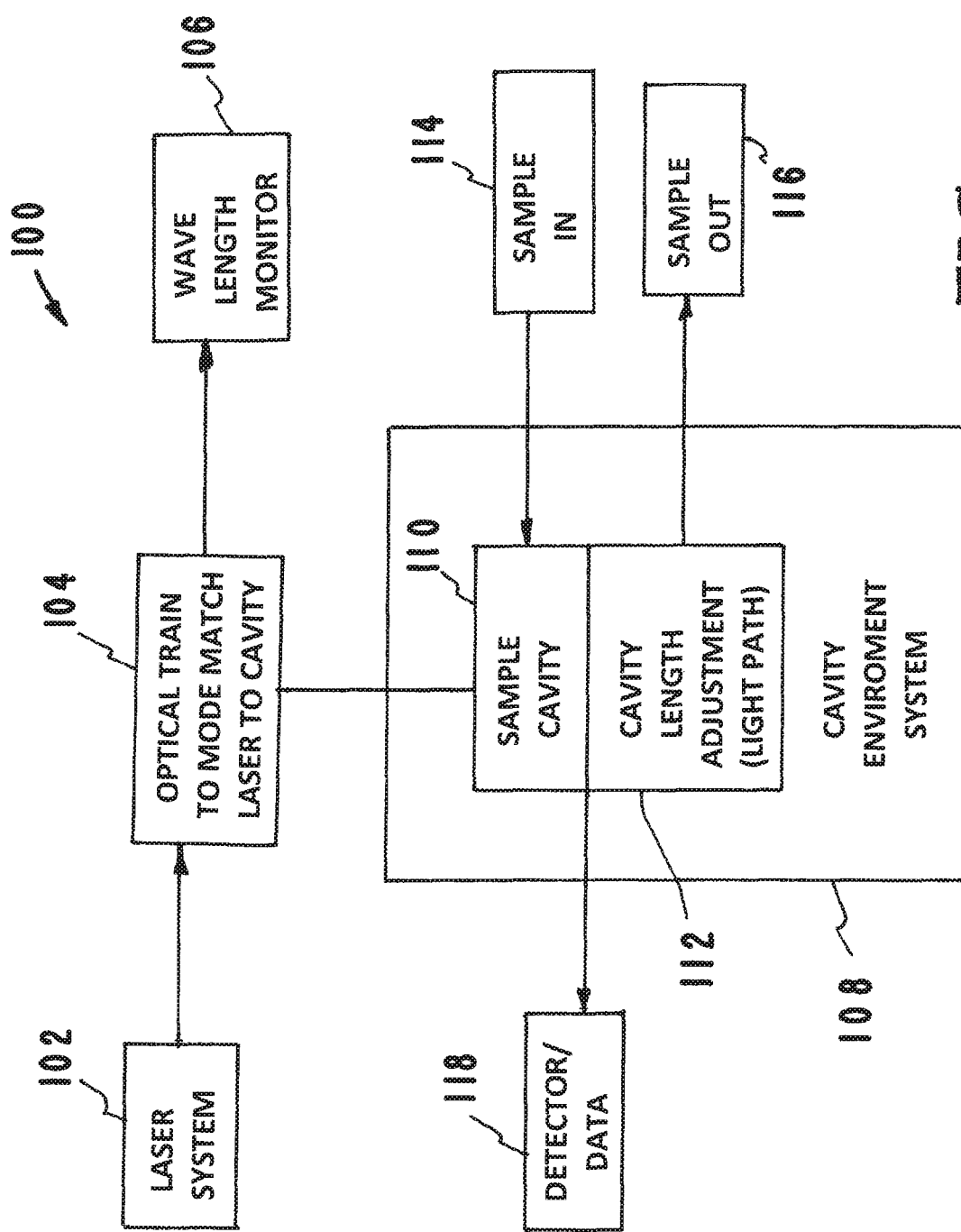
FIG. 1 is an illustrative flow chart that illustrates features of the disclosed apparatus, systems, and methods.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Statement of the Problem

This work pertains to quantitative optical absorption spectroscopy, specifically as it is used to determine the molar mixing ratio of a molecular species of interest in a gaseous sample. The specific goal of this work is the determination of the mole fraction of $^{14}C$ in a sample of carbon-containing gas such as carbon dioxide, carbon monoxide, or methane. While the general principles of quantitative optical spectroscopy are well known, the extremely low abundance of $^{14}C$ in nature, on the order of $10^{-12}$ for modern samples of natural origin (i.e. not isotopically enriched), makes the optical measurement of $^{14}C$ mole fraction considerably more difficult than mole fraction measurements of more common molecular species. The rarity of $^{14}C$ results in difficulties due to low signal-to-noise ratio and also difficulties due to low signal-to-background ratio. For applications in biochemical research that start with compounds artificially enriched in $^{14}C$, which are the kinds of applications the inventors presently envision for the optical $^{14}C$ analyzer, the precision required to make a useful $^{14}C$ measurement is on the order of one-tenth of the modern natural abundance.

Signal-to-noise refers to the ratio of the optical absorption due to the molecular species of interest to the random fluctuations (noise) affecting the absorption measurement that are inherent to all physical measurements. Noise includes fluctuations of a fundamental nature, such as shot noise in optical power measurements, as well as "technical" noise such as undesirable variations in the intensity and frequency of light sources, optical detector noise in excess of the shot-noise limit, and the like. The signal-to-noise ratio places a limit on the smallest concentration of the species of interest that can be detected in any sample.

Even if the absorption signal from the molecules of interest have a signal-to-noise ratio that is in principle adequate for detection, practical measurements may be impractical due to poor signal-to-background ratio. This arises when other optically absorbing species are present in the same sample as the molecules of interest, resulting in background absorption, or interference, which is indistinguishable from the absorption of the molecules of interest. Spectroscopic interference can arise from molecules which are chemically distinct from the molecular species of interest or from chemically identical molecules having different isotopic composition (isotopologues). Isotopologues present a particularly difficult problem; unlike chemically distinct molecules, which can often be isolated via a purification process or spectroscopically separated by optical frequency, isotopologues of the analyte species are not easily and effectively separated chemically or spectroscopically. In the case of specific interest to us, the quantification of $^{14}C$ mole fraction, the $^{14}C$ atoms must be incorporated in some gaseous molecule. Carbon dioxide is a particularly attractive molecule in which to measure the isotopic composition of carbon. In this case the absorption of the interesting $^{14}C^{16}O_2$ isotopologue must be distinguished from interference due to other molecules which might be present in samples of natural origin, such as water vapor ($H_2O$), methane ($CH_4$), nitrous oxide ($N_2O$), carbon monoxide (CO) and ozone ($O_3$), as well as interference from other isotopologues of $CO_2$ itself. Since carbon has two stable isotopes and oxygen three, there are 12 stable isotopologues that are all optically active in the same general wavelength region as the $^{14}C^{16}O_2$ isotopologue. Even the rarest of the stable isotopologues of $CO_2$ is approximately 1000 times more abundant than $^{14}C^{16}O_2$ in natural samples; the more common isotopologues are present in concentrations a billion to a trillion times more abundant than $^{14}C^{16}O_2$. It is the combination of a very weak signal with interference from a background which is much stronger than the signal itself which makes the optical quantification of $^{14}C$ abundance exceptionally difficult.

Solution: Signal-to-Noise Optimization

The weakness of molecular absorption arising from $^{14}C$ suggests the combination of cavity-enhanced spectroscopy and sample purification to achieve an acceptable signal-to-noise ratio. Cavity-enhanced absorption spectroscopy is capable of achieving sensitivity approaching the shot noise limit, the fundamental limit for optical absorption measurements with classical light or conventional laser light sources. Of the many variants of cavity-enhanced spectroscopy, cavity ring-down spectroscopy (CRDS) appears to be the preferred implementation, because it is insensitive to laser technical noise and has been shown to be a robust technology for practical applications. Other implementations could also be considered, however. In particular, recent research has shown that some interferences in CRDS can be mitigated by measuring both linear and saturated absorption. Such a data analysis could be used in the context of the work described here.

The absorption signal of interest is a maximum if the gas sample is converted to a pure chemical species, so that there is no dilution of the $^{14}C$ signal by extraneous gas components. In the context of signal-to-noise optimization, relatively coarse purification is all that is required, for instance purification of $CO_2$ to a purity of 99% would provide essentially as much $^{14}C$ signal as one could ever achieve. However, signal-to-background considerations may require much better sample purification.

Non-gaseous target samples must first be combusted to a gaseous state for resonant molecular spectroscopy to be employed. Samples are flash combusted then reduced. In the case where the desired $^{14}C$ species is carbon dioxide, samples are stoichiometrically combusted in pure oxygen, and a three-way catalytic converter reduces trace amounts of carbon monoxide and mono-nitrogen oxides to carbon dioxide and dinitrogen respectively. For carbon monoxide, the carbonaceous sample is pyrolyzed over an oxidant (e.g. CuO) and then electrochemically reduced to carbon monoxide. For methane, combusted samples are methylated using a nickel catalyst on an activated alumina substrate.

Signal-to-noise considerations also strongly limit the selection of an absorption line for the optical measurement of $^{14}C$. For the example of carbon dioxide as the carbon-carrying gas, only the strongest rotational components of the fundamental infra-red active vibrational bands ($\textcircled{v}_1$ and $\textcircled{v}_3$) are logical candidates for an optical absorption measurement. Calculations based on the valid assumption that the oscillator strengths of the $^{14}C^{16}O_2$ lines are essentially as the same as those of the analogous $^{12}C^{16}O_2$ lines indicate that for reasonable sample conditions, the peak absorption coefficient due to the $^{14}C^{16}O_2$ isotopologue in pure $CO_2$ is large enough to be measured by CRDS with adequate precision for biological applications.

Solution: Signal-to-Background Optimization

As explained above, adequate signal-to-noise ratio alone does not suffice for a practical measurement of $^{14}C$ if the absorption arising from $^{14}C$ cannot be distinguished from that due to interfering molecular spectra. A combination of strategies can be used to deal with interferences, depending on their origins. In the neighborhood of the $^{14}C^{16}O_2$ asymmetric stretch band ($v_3$), the one that appears to have the greatest practical potential for optical analysis, there are also absorption bands due to molecules present in normal ambient air, including $H_2O$, $O_3$, $N_2O$, $CO$, and $CH_4$. The inventors have modeled the interference due to known absorption lines of these species, taken from the Hitran data base and determined the concentration levels of these molecules for which spectroscopic interferences could affect the measurement of $^{14}C$. An important first step to improve signal-to-background is to purify the $CO_2$ sample to minimize the interference from foreign species. Interference from species such as nitrous oxide, carbon monoxide, carbon dioxide, water, ozone, methane, and all stable isotopes thereof can be removed or mitigated using chromatographic, membrane, and/or cryogenic purification processes. Each of these methods leverages differences in physical properties between the target and interfering species: chromatographic separations use differences in partition coefficients (this could also be conducted with liquid, and dissolved solid samples before combustion), membrane purification processes take advantage of physical size differences, and cryogenic methods exploit differences in condensation and sublimation temperatures.

For some foreign molecules, careful sample preparation should be adequate to reduce spectroscopic interference to an acceptable level. Other molecules may be more problematic because they are difficult to completely remove and their lines have exceptionally large oscillator strengths ($N_2O$ and $CO$ are such cases). To deal with these cases, the inventors have developed the procedure of fitting experimental spectroscopic data (spectrograms) to a spectral model. The spectral fitting procedure begins with the acquisition of high-resolution spectra of the potentially interfering species in a pure form and under known sample conditions. From analysis of these spectra, all the absorption lines that can potentially interfere with the $^{14}C$ measurement are described by well-defined mathematical functions, based on molecular line shape theory, and including parameters that describe the influence on the interfering spectrum of such factors as the concentration(s) of the interfering species, sample pressure, and sample temperature. A spectral model is constructed, which describes the optical absorption in the neighborhood of the $^{14}C$ absorption line and includes the $^{14}C$ line and all of the interfering species, with their concentrations as free parameters. When analyzing the $^{14}C$ content of a gas sample, spectrograms are acquired over a wavelength range that includes not only the absorption line due to $^{14}C$, but also absorption from the potential interfering species. A fitting procedure based on non-linear least-squares minimization is applied to find the values of the free parameters in the spectral model such that the model is in best agreement with the measured data (e.g., in the sense of minimum rms deviation). The result of this fitting procedure is the optical absorption due to $^{14}C$ with all background absorption from interfering species properly taken into account. Numerical modeling shows that provided the experimental spectrogram has enough data points to constrain all the free parameters of the spectral model, and provided that all physically relevant variables are parameterized in the model (all interfering species, as well as any other experimental variables which may change during the course of the experiment) the mole fraction of $^{14}C$ can be determined with a precision that is not considerably worse than the limit imposed by the experimental signal-to-noise ratio, even when the signal-to-background ratio is extremely small, as small as 0.001.

Of the molecules that contribute to the background of the $^{14}C^{16}O_2$ spectrum, a special role is assumed by carbon dioxide itself. Of the twelve stable isotopologues of $CO_2$, there are some six that absorb appreciably in the neighborhood of $^{14}C^{16}O_2$ (depending on the particular $^{14}C^{16}O_2$ line under consideration). They are chemically identical to the species being measured and cannot be removed by isotopic separation without falsifying the intended $^{14}C$ mole fraction measurement. Still, the same two strategies that have been described for dealing with interference from foreign molecules can be employed to minimize interference from the stable isotopologues of $CO_2$. The first approach, analogous in a way to the removal of foreign gases, is to reduce as much as possible the optical absorption due to stable isotopologues that interfere with $^{14}C^{16}O_2$. This is possible by carefully selecting the temperature and pressure of the gas in the analyzer. Pressure affects above all the widths of the molecular absorption lines, and it is the non-vanishing line width that leads to overlap of different spectral lines in the complete molecular spectrum. Reducing the sample pressure reduces all the molecular line widths, and consequently reduces the background of the stable isotopologues at the frequency of the $^{14}C^{16}O_2$ line. The absorption line width is approximately proportional to pressure when the pressure exceeds about 10-20 Torr (the precise pressure varies from one line to another) and approximately constant below that pressure. Consequently reducing the sample pressure to a value preferably below about 75 Torr (and more preferably in the range of 10-20 Torr) is advantageous. Temperature affects the molecular lines widths slightly, but has a much greater effect on the absorption intensity due to the temperature-dependent distribution of the molecular population amongst the quantized molecular energy levels. For gases in thermal equilibrium (valid for our samples) this distribution is described by the Maxwell-Boltzmann law, which relates the population in a given quantum state to the energy level (term value) of that state. The $^{14}C^{16}O_2$ lines that are suitable for a measurement of mole fraction all originate on levels only slightly more energetic than the ground state; these are the strongest rotational components of the band. The bands of the other isotopologues are shifted in frequency due to the differences in mass of the carbon and oxygen atoms, and consequently the lines that can interfere with the $^{14}C^{16}O_2$ line of interest always originate on energy levels that are more energetic—generally much more energetic—than the $^{14}C^{16}O_2$ line. Consequently the intensities of the interfering lines are greatly reduced with respect to the $^{14}C^{16}O_2$ line when the sample temperature is reduced. The only fundamental lower limit to the sample temperature is the sublimation temperature of $CO_2$ at the operating pressure (which would give a preferred temperature range of between about −120 C and about 0 C), but experience shows that an alignment-sensitive optical apparatus should be subjected to the smallest practical excursions in temperature. Numerical modeling of simulated spectra indicates that, depending on the exact choice of the $^{14}C^{16}O_2$ line, the advantages of sample temperature reduction may be realized at a temperature as high as about +5° C.

The spectroscopic interference of the stable isotopologues of $CO_2$ cannot be completely removed, consequently the spectral fitting procedure should also discriminate the $^{14}C^{16}O_2$ line from background absorption. The principles involved are exactly the same for interference from isotopologues of $CO_2$ as for interference from foreign gas species. To develop a spectral model, spectra can be acquired from isotopically purified samples, to identify the isotopic origin of the lines in the natural spectrum. The extensive literature on the spectroscopy of $CO_2$ is also available for this purpose. Of course, each isotopologue must be treated as an independent species, and the natural variability of stable isotope ratios must be taken into account. Modeling of simulated spectra indicates that spectrograms of the $^{14}C^{16}O_2$ region contain enough information to adequately constrain the isotopic composition of the sample.

In dealing with spectroscopic interferences, it is not necessary to impose the restriction that all spectroscopic information be acquired in a single spectrogram that includes the $^{14}C^{16}O_2$ line. Multiple spectroscopic measurements can be used to constrain the sample composition, and these spectra can be acquired either with the same apparatus that acquires the $^{14}C^{16}O_2$ spectrum or in ancillary measurements with other spectrometers. For instance, the concentrations of $N_2O$ and CO can be determined very precisely by mid-IR spectroscopy, possibly using the same spectrometer that measures absorption due to $^{14}C$, and the isotopic ratios $\delta(^{13}C/^{12}C)$ and $\delta(^{18}O/^{16}O)$ can be determined by either mid-IR or near-IR spectroscopy. If such ancillary measurements are used, the basic method of fitting the experimental spectrogram to a spectral model is the same as described above, but the results of the ancillary measurements (e.g. the CO concentration of the sample or the measured abundances of stable carbon and oxygen isotopes) are used to preset model parameters to precisely known values in order to improve the precision of the least-squares adjustment of the $^{14}C^{16}O_2$ absorption coefficient.

Quantitation of Radiocarbon in Biological Samples

Radiocarbon ($^{14}C$) is a commonly used isotope in biomedical research. Hundreds of peer reviewed manuscripts are published every year using radiocarbon and thousands of clinical assays are preformed every year that rely on radiocarbon. Methods to quantify radiocarbon are in routine use but most rely on decay counting which requires either high isotope levels or unreasonably long counting times to obtain adequate data. Studies often require levels of labeled agents in test systems that are well outside the natural concentration of the metabolite or biological molecule in the cell thus changing the biological process targeted for measurement. In addition, many studies require use of isotope levels that can impart radiological damage to the test system, which limits or precludes use in human studies. Finally, disposal of the radiolabeled samples and reagents is problematic and costly. Significant demand continues to exist for methods that reduce the requirement for unnaturally high levels of isotope or large samples.

Accelerator Mass Spectrometry (AMS) is currently the most sensitive method for quantitation of radiocarbon in biological samples. AMS can routinely quantify an attomole of radiocarbon-labeled agent with a precision of around 1% in real samples. This technology has been used in a variety of studies over the last 20 years where very high sensitivity is needed. Examples where AMS has allowed studies to be conducted that were not possible without it are in risk assessment where data is needed for low dose exposures such as for compounds that are in low mass in food or air; in drug development where compounds are either highly potent and have low bioavailability; where systemic distribution is not desired; where samples are extremely small and in cases where test agents are only available in low specific activity. More recently interest has grown on the use of such technology to conduct early human studies where drug or toxicant doses are kept extremely low to limit the potential for safety liabilities. Such studies have been growing to allow faster testing of new therapeutic entities in humans, for validation of model systems for humans, and for risk extrapolation between animal models and humans. Continued growth is expected, particularly in pharma due to new guidance from FDA for conducting microdosing studies and from the ICH recommendation for preclinical safety testing of new therapeutic entities.

Accelerator mass spectrometry is a type of isotope ratio mass spectrometry. Within a sample, the amount of a rare isotope (i.e., $^{14}C$) is measured relative to a more abundant isotope (i.e., $^{13}C$ or $^{12}C$). Absolute quantitation is provided by comparing the measured isotope ratio of the sample to the measured isotope ratio of a well-defined standard. In the biosciences, AMS was originally applied to overcome limitations in detection sensitivity of decay counting for studying the molecular damage caused by exposure to low levels of environmental carcinogens and pollutants. By counting individual atoms, AMS quantitatively measures $^{14}C/C$ isotope ratios and has a sensitivity of $-10^6$ $^{14}C$ atoms—corresponding to attomole quantities of $^{14}C$. Using AMS detection, activities of $^{14}C$-labeled agents as low as a few nCi/person can be used to assess metabolism, and activities as low as 100 nCi/person can be used to address macromolecular binding in the study of candidate drugs or toxicants. This level of radioactivity is less than that from a single day's exposure to background ionizing radiation, or from a chest x-ray.

AMS instrument costs are on the order of several millions of dollars and they still require support from a highly trained technical staff and location in specialized facilities. Additionally, traditional AMS ion sources require that the sample be presented as a solid graphitic target. This necessitates the time-consuming conversion of carbonaceous material to graphite in a technically complex procedure that limits overall measurement throughput and can keep per sample charges unreasonably high. On average, one technician can prepare 120 samples for analysis in a day through a multi-step process that takes a minimum of 36 hours. This requires expert knowledge and specialized facilities which are only available at a very few places in the country. Development of a method that has a footprint of a few square feet and that can be operated without the need for a staff of trained operators and physicists, without the need for expensive and large instrumentation is a gap that, if filled, would open new avenues of research and clinical studies by its low cost, ease of use and broad availability.

Quantification of $^{14}C$ via optical spectroscopy offers an approach that eliminates many of the shortcomings of an accelerator-based system. This technique can exploit the selectivity of the ro-vibrational transitions in the infrared spectral region or the ro-vibronic transitions in the ultraviolet and their isotopic shifts. The sensitive infrared-based approaches all utilize multipath cells or intra-cavity laser techniques to increase the optical path-length. The more sensitive of these techniques now include Cavity Ring Down Spectroscopy (CRDS). Sensitive electronic excitation approaches utilize fluorescence detection that exploit the signal-to-noise advantage of signal photons emerging from a null background.

Cavity Ring-Down Spectroscopy (CRDS)

CRDS is a proven technique for detecting trace quantities of gases. CRDS with near-infrared lasers is an established method for trace gas analysis, and has been widely adopted in the greenhouse gas monitoring community. More recently, Picarro Inc. (Santa Clara, Calif.) has embarked upon a commercial development program to extend CRDS into the mid-infrared region of the spectrum. The first prototype from this program, an isotopic $N_2O$ analyzer. The following year, the design underwent a major revision, including many performance improvements.

In CRDS, the beam from a single-frequency, laser diode enters a cavity defined by two or more high reflectivity mirrors. When the laser is on, the cavity quickly fills with circulating laser light. A fast photodetector senses the small amount of light leaking through one of the mirrors to produce a signal that is directly proportional to the intensity in the cavity. When the photodetector signal reaches a threshold level (in a few tens of microseconds), the laser is abruptly turned off. The light already within the cavity continues to bounce between the mirrors but steadily leaks out and decays to zero in an exponential fashion. This decay, or "ring down", is measured in real-time by the photodetector and the amount of time it takes for the ring down to happen is determined solely by the reflectivity of the mirrors (for an empty cavity). However, if a gas species that absorbs the laser light is introduced into the cavity, a second loss mechanism within the cavity (absorption) is now introduced. This accelerates the ring down time compared to a cavity without any additional absorption due to a targeted gas species and allows for quantitation of the concentration of the absorbing gas.

Several aspects of this measurement approach merit further examination. First, CRDS measures the cavity ring down time. This time-based measurement is independent of initial recorded laser intensity. As such it is immune to drifts in laser performance and photo-detector response. This is key to both the low noise of floor of CRDS as well as its low-drift and hence its ability to provide quantitative accuracy for weeks and months between re-calibration. In addition, the same wavelength scanning used to measure the absorption line is used to scan several points on the baseline. This accurate baseline measurement eliminates the need for a zero gas to calibrate performance.

Another key aspect of CRDS is the relatively strong signal due to the long effective path-length. Depending on the reflectivity of the cavity mirrors, light can circulate in the cavity for tens of microseconds before decaying to zero, producing an effective path length of tens of kilometers through the sample. Much like a multi-pass cell, this very long effective path length gives CRDS its extremely high sensitivity. In spite of the high mirror reflectivity, the light intensity inside the ring-down cavity is well below the saturation intensity of the target $CO_2$ lines. Thus, the absorption responds linearly to the analyte concentration.

Because the temperature and pressure of the CRDS cavity is precisely known and actively stabilized, the measured intensity of each absorption line is linearly proportional to the gas concentration. The relative isotopic abundances can then be derived in a direct manner from the ratios of the observed line strengths.

The absorption lines that we measure are the ro-vibrational asymmetric stretch modes of the O═C═O molecule, in which the central carbon atom is moving along the bond axis and 180 degrees out of phase with the two oxygen atoms. This is a strongly infrared active mode. For the strongest of the $^{12}CO_2$ absorption lines, at 2335.919 $cm^{-1}$, the absorption at 15 Torr pressure and 100% concentration is about $2.1 \times 10^8$ ppm/cm. The vibrational transition is split into a large number of separate rotational lines, separated from each other by about 1-2 $cm^{-1}$.

One Embodiment of Inventor's Apparatus, Systems and Methods

Referring now to the drawings and in particular to FIG. 1, the disclosed apparatus, systems, and methods are illustrated. The apparatus, systems, and methods are designated generally and collectively by the reference numeral 100. Referring again to FIG. 1, an illustrative flow chart provides information about one embodiment of the inventor's apparatus, systems, and methods which are designated generally by the reference numeral 100. The schematic shows the following structural components and steps:

the laser system 102,
the optical train to mode match laser to cavity 104,
the wavelength monitor 106,
the cavity environment system 108,
the sample cavity 110,
the cavity length adjustment (light path) 112,
the sample in 114,
the sample out 116, and
detector/data 118.

The structural components and steps of the apparatus, systems, and methods 100 having been describe the operation will now be considered. The laser system 102, optical train to mode match laser to cavity 104, and wavelength monitor 106 direct laser light into the sample cavity 110. The sample cavity 110 is maintained at the desired environmental conditions by the cavity environment system 108. The sample is introduced to the sample cavity 110 by the sample in component 114.

The laser is used to illuminate the optical cavity 110, which in its simplest form includes reflective mirrors. The laser system 102 is then turned off in order to allow the measurement of the exponentially decaying light intensity leaking from the cavity 110. During this decay, light is reflected back and forth between the mirrors giving an effective path length. The "ringdown time" is used to calculate parameters of the absorbing substance in the gas mixture 114 in the cavity.

The cavity environment system 108 maintains the sample cavity 110 at the desired environmental conditions. The cavity length adjustment (light path) 112 component provides closed-loop scheme for cavity length (light path) control.

Optical Spectrometer for Analysis of Carbon-14

Figure 2:
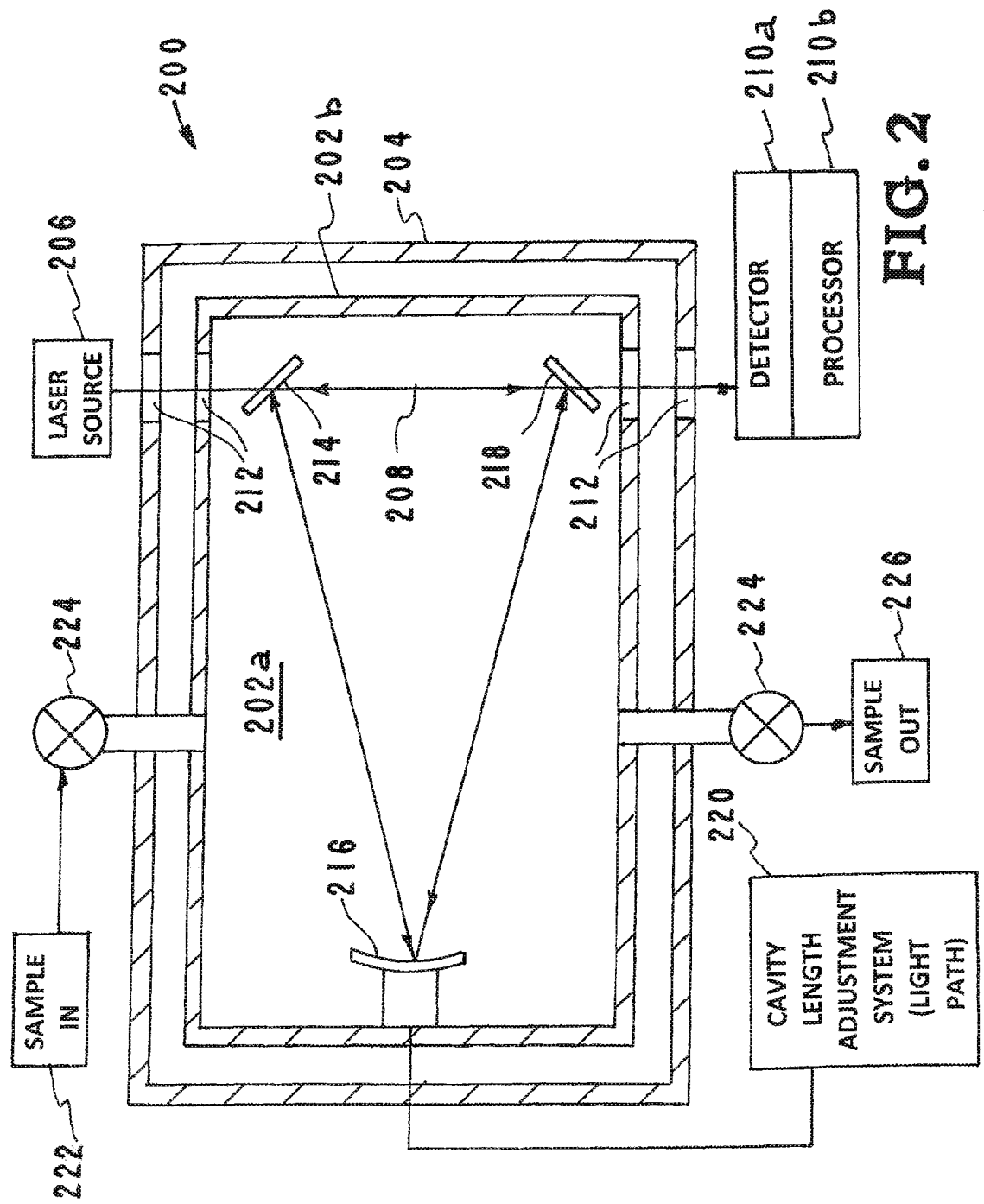
FIG. 2 is a schematic that illustrates additional features of the disclosed apparatus, systems, and methods.

Referring now to FIG. 2, additional features of the disclosed apparatus, systems, and methods are illustrated. FIG. 2 includes the following components:

an optical spectrometer 200,
a resonant optical cavity 202*a*,
cavity housing 202*b*,
cavity environment housing 204,
an optical source 206,
optical radiation 208,
an optical detector 210*a*,
a processor 210*b*,
optical windows 212,
1st mirror 214,
2nd mirror 216,
3rd mirror 218,
cavity length adjustment system (light path) 220,
a sample gas (sample) in 222,
valve 224, and
sample out 226.

The structural components of the optical spectrometer 200 having been described the operation of the optical spectrometer 200 will now be considered. The optical source 206 directs the optical radiation 208 through the optical windows 212 into the cavity 202*a* within the housing 202*b*. The cavity housing 202*b* is maintained at the desired environmental conditions by the cavity environment system in the cavity environment system 204. The sample is introduced to the sample cavity 202*a* by the "sample in" component 222.

The optical source 206 in specific embodiments a laser beam) illuminates the cavity 202*a*. The optical radiation 208 is reflected by mirrors 214, 216, and 218. The optical source 206 is then turned off in order to allow the measurement of the exponentially decaying light intensity leaking from the cavity 202*s*. During this decay, light is reflected back and forth between the mirrors giving an effective path length. The "ringdown time" is used to calculate parameters of the absorbing substance in the gas mixture in the cavity.

The cavity environment system 204 maintains the sample cavity 202*a* at the desired environmental conditions. The cavity environment system 204 in one embodiment is a freezer. The cavity length adjustment (light path) 220 component provides closed-loop scheme for cavity length (light path) control. The cavity length adjustment (light path) 220 component in one embodiment is a piezoelectric crystal.

Cavity ring-down spectrometers (CRDS) are used for the measurement of trace gases. The disclosed apparatus, systems, and methods are the first application of this technology to measure 14$CO_2$ in biochemical samples that are at levels close to the natural isotopic abundance for this isotope. The disclosed apparatus, systems, and methods are expected to replace liquid Scintillation Counting, as well as Accelerator Mass Spectrometry (in certain instances). The disclosed apparatus, systems, and methods provide a table-top sized laser-based spectroscopic system to quantify $^{14}C/^{12}C$ ratios from $CO_2$ and CO. The apparatus, systems, and methods 200 provide a laser spectroscopic system capable of quantifying $^{14}C/^{12}C$ ratios at natural isotopic abundances.

The disclosed apparatus, systems, and methods provide a cavity ring-down spectrometer (CRDS) for the measurement of carbon-14 and other isotopes including $^{13}C$ and $^{12}C$. In various embodiments the apparatus, systems, and methods quantify the amount of $^{14}C$ derived from biochemicals using the optical spectroscopic technique of cavity ring down spectroscopy (CRDS). In the disclosed apparatus, systems, and methods biomolecules labeled with $^{14}C$ are combusted to $CO_2$ gas which is directed into a cavity. A laser, operating in the mid IR range, is used to measure the amounts of $^{14}C$, $^{13}C$ and $^{12}C$ by recording the ring down time at several wavelengths.

Ring-Down Event Example

Figure 3:
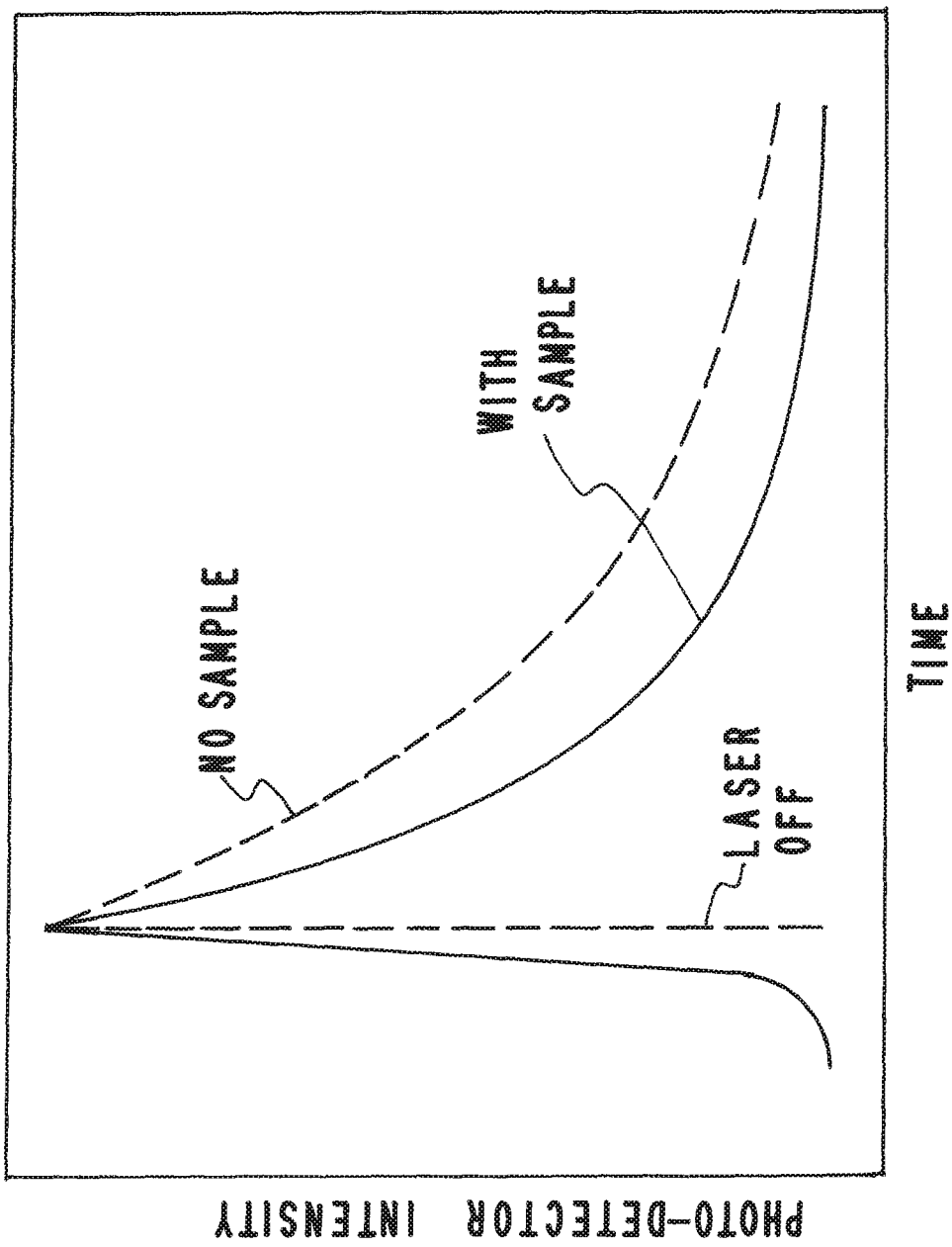
FIG. 3 is a graph that illustrates an example ring-down event.

Referring now to FIG. 3, a graph illustrates an example ring-down event. The decay line labeled "empty cavity" illustrates a base line measurement without the sample. The decay line labeled "with sample" illustrates represents a decay with additional sample loss.

Single Laser, Model-Based, Closed-Loop Cavity Length Control

Figure 4:
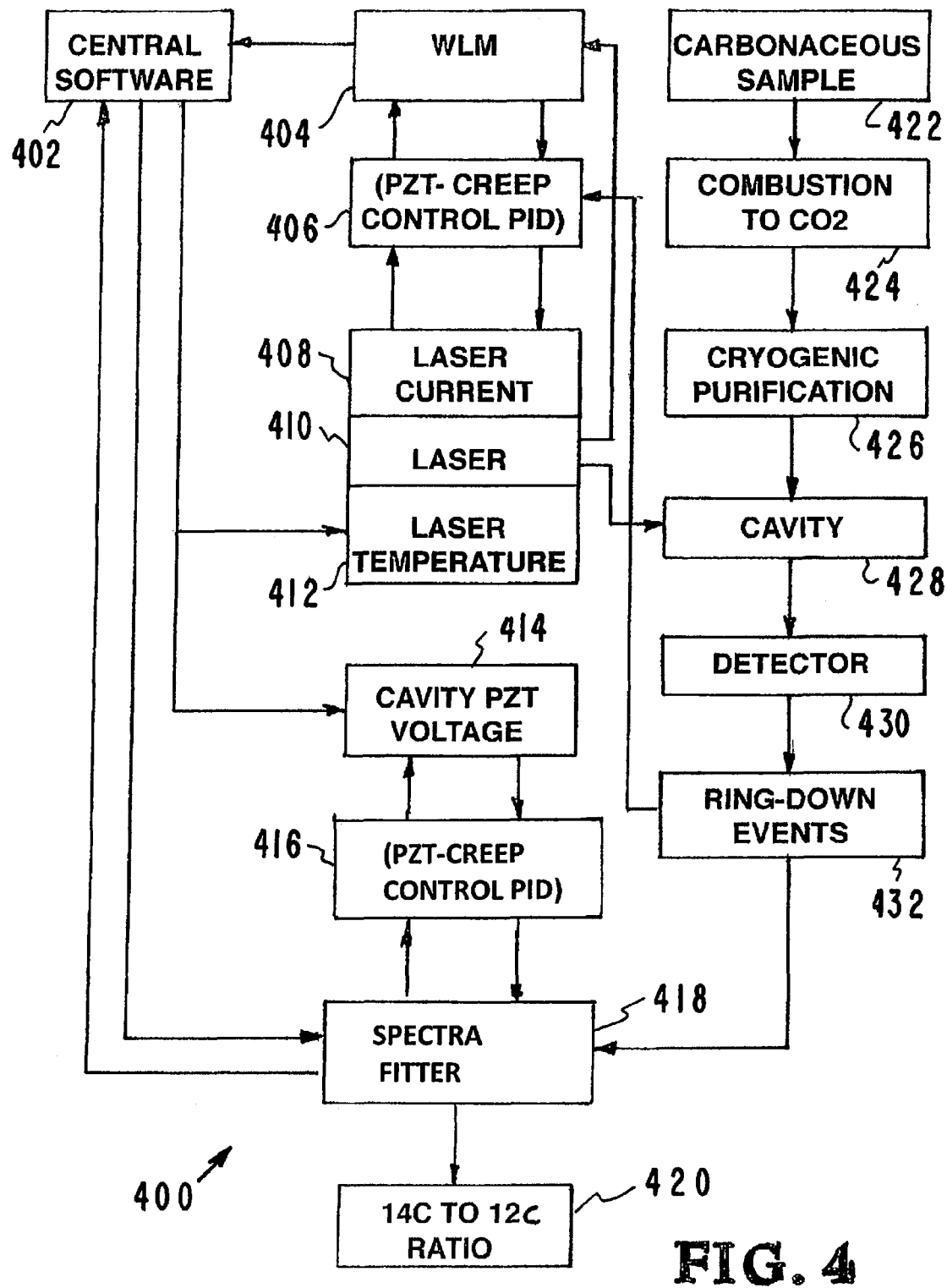
FIG. 4 is a flow chart that illustrates additional features of the disclosed apparatus, systems, and methods.

Referring now to FIG. 4, a flow chart illustrates a single laser, model-based, closed-loop scheme for cavity length control. Cavity ring-down spectrometers typically employ a PZT stack to modulate the cavity transmission spectrum. While PZTs ease instrument complexity and aid measurement sensitivity, PZT hysteresis hinders the implementation of cavity-length-stabilized, data acquisition routines. Once the cavity length is stabilized, the cavity's free spectral range imparts extreme linearity and precision to the measured spectrum's wavelength axis. Additional information about the single laser, model-based, closed-loop scheme for cavity length control shown in FIG. 4 is provided in the article: "A New Accelerator Mass Spectrometry System for $^{14}C$-quantification of Biochemical Samples," by Ted J. Ognibene, Graham Bench, Tom A. Brown, Graham F. Peaslee, and John S. Vogel, in International Journal of Mass Spectrometry 218 (2002) 255-264, is incorporated herein in its entirety by this reference.

The inventor's apparatus, systems, and methods illustrated in FIG. 4 are designated generally and collectively by the reference numeral 400. Referring again to FIG. 4, the flow chart shows the following structural components and steps:

- 402—Central Software,
- 404—WLM (Wavelength Monitor),
- 406—PZT—Creep Control (PID),
- 408—Laser Current,
- 410—Laser,
- 412—Laser Temperature,
- 414—Cavity PZT Voltage
- 416—(PZT—Creep Control PID),
- 418—Spectra Fitter,
- 420—$^{14}C$ to $^{12}C$ Ratio
- 422—Carbonaceous Sample,
- 424—Combustion to $CO_2$,
- 426—Cryogenic Purification,
- 428—Cavity,
- 430—Detector, and
- 432—Ring-Down Events.

The inventor's apparatus, systems, and methods 400 having been illustrated and describe the operation will now be considered. The inventor's apparatus, systems, and methods illustrated in the flow chart 400 provide background correction for the required precision to quantify the amount of $^{14}C$ derived from biochemicals using cavity ring down spectroscopy (CRDS). The inventor's apparatus, systems, and methods illustrated in the flow chart 400 provide an optical spectrometer for analysis of carbon-14 that includes a resonant optical cavity configured to accept a sample gas including carbon-14; an optical source configured to deliver optical radiation to the resonant optical cavity; an optical detector configured to detect optical radiation emitted from the resonant cavity and to provide a detector signal; and a processor configured to compute a carbon-14 concentration from the detector signal; wherein computing the carbon-14 concentration from the detector signal includes fitting a spectroscopic model to a measured spectrogram; wherein the spectroscopic model accounts for contributions from one or more interfering species that spectroscopically interfere with carbon-14.

Additional features of the inventor's apparatus, systems, and methods include the previously described optical spectrometer wherein the interfering species have greater concentration in the sample gas than the concentration of carbon-14 in the sample gas. The previously described optical spectrometer wherein the rare species has an abundance of 1000 parts per trillion or less in the gas sample, and wherein the carbon-14 concentration in the gas sample is quantified with a precision of 10% of the abundance or better. The previously described optical spectrometer wherein the optical spectrometer is further configured to reduce spectroscopic interference by operating at a sample gas temperature between about $-12°$ C. and about $0°$ C. The previously described optical spectrometer wherein the optical spectrometer is further configured to reduce spectroscopic interference by operating at a sample gas pressure of about 75 Torr or less. The previously described optical spectrometer wherein the optical spectrometer is further configured to reduce spectroscopic interference by processing and/or purifying an input sample gas to deliver a processed sample gas to the resonant optical cavity. The previously described optical spectrometer wherein the processing the input sample gas comprises a method selected from the group consisting of: chromatography, passage through species selective membranes, passage through a cold trap, and combustion in a combustion reactor. The previously described optical spectrometer wherein the processing the input sample gas comprises reducing concentrations of one or more interfering species selected from the group consisting of: $N_2O$, $CO$, $CO_2$, $H_2O$, $O_3$, $CH_4$, and all stable isotopes thereof. The previously described optical spectrometer wherein the interfering species include one or more species chemically distinct from a carbon-14 containing species being measured. The previously described optical spectrometer wherein the interfering species include one or more isotopologues distinct from a carbon-14 containing isotopologue being measured.

The optical spectrometer in one embodiment includes a sample preparation unit configured to convert a biological sample to the sample gas. The previously described optical spectrometer wherein the sample preparation unit comprises a combustion chamber having carbon dioxide as the relevant species in the sample gas. The previously described optical spectrometer wherein the sample preparation unit comprises a reduction chamber having carbon monoxide as the relevant species in the sample gas. The previously described optical spectrometer wherein the sample preparation unit comprises a chemical reactor having methane as the relevant species in the sample gas. The previously described optical spectrometer wherein the optical spectrometer is further configured to compensate for spectroscopic interference by determining concentrations of one or more of the interfering species via one or more auxiliary concentration measurements and using results from the auxiliary concentration measurements when fitting the spectroscopic model. The previously described optical spectrometer wherein a time constant for an exponential decay in time is determined from the detector signal. The previously described optical spectrometer wherein the time constant is used to determine an absorbance of the sample gas. The previously described optical spectrometer wherein the detector signal is analyzed to provide separate linear absorbance and saturated absorbance terms.

Amount of 14C Derived from Biochemicals Quantified

Figure 5:
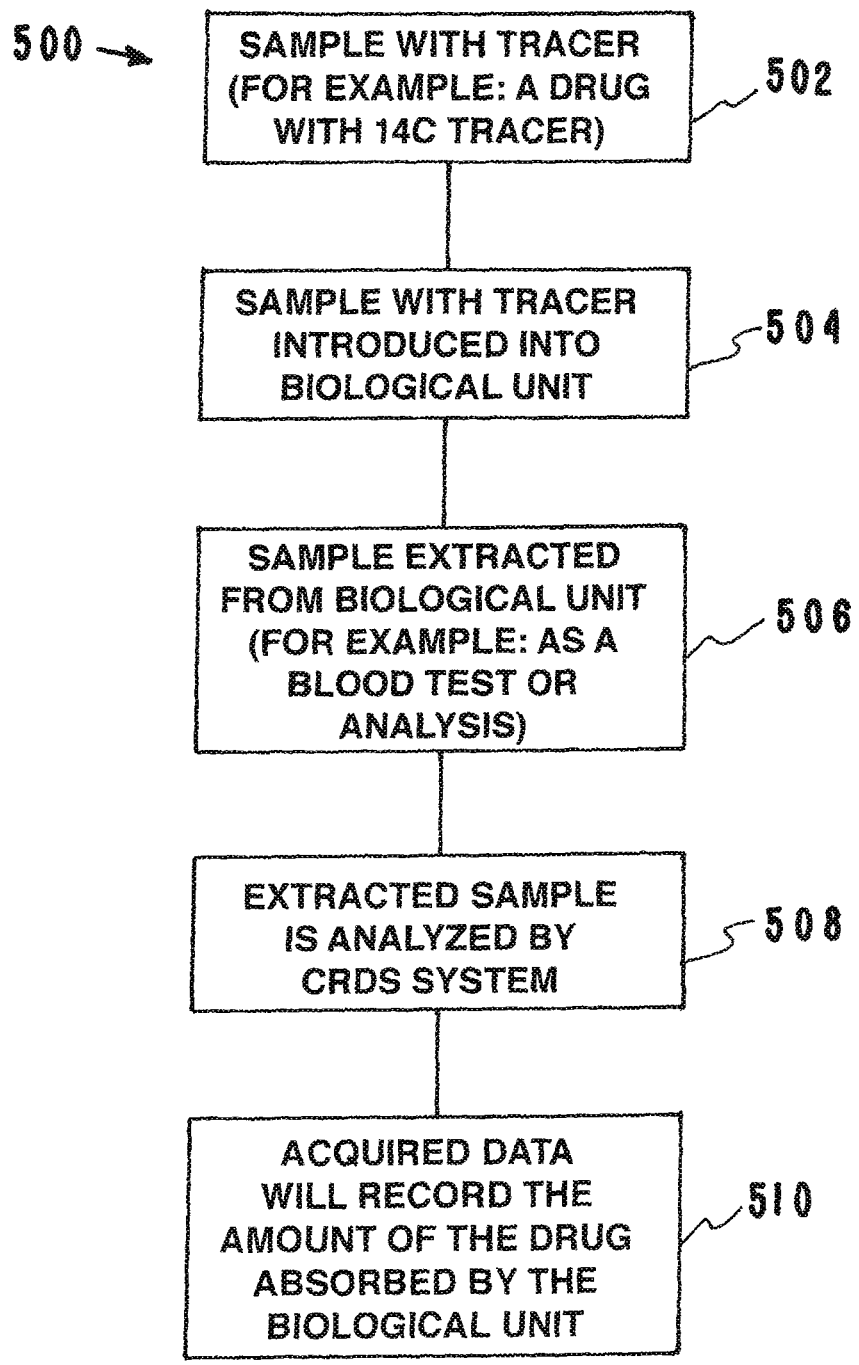
FIG. 5 is a flow chart that illustrates additional features of the disclosed apparatus, systems, and methods.

Referring now to FIG. 5, another embodiment of the disclosed apparatus, systems, and methods is illustrated by a flow chart. This embodiment of the apparatus, systems, and methods is designated generally by the reference numeral 500. The embodiment 500 provide a cavity ring-down spectrometer (CRDS) scheme for the measurement of carbon-14 and other isotopes including 13C and 12C. In this embodiment the scheme quantifies the amount of 14C derived from biochemicals using the optical spectroscopic technique of cavity ring down spectroscopy (CRDS).

Referring again to FIG. 5, additional information about the disclosed apparatus, systems, and methods is illustrated by a flow chart. The flow chart is designated generally by the reference numeral 500. The flow chart 500 illustrates a cavity ring-down spectrometer (CRDS) scheme for the measurement of carbon-14 and other isotopes including 13C and 12C. In this scheme the amount of 14C derived from biochemicals using the optical spectroscopic technique of cavity ring down spectroscopy (CRDS) is quantified. Referring again to FIG. 5, the flow chart shows the following steps: 502—sample with tracer (for example a drug with 14C tracer), 504—sample with tracer introduced into biological unit, 506—sample extracted from biological unit (for example: ASA blood test or urinalysis, 508—extracted sample is analyzed by CRDS system, and 510—acquired data will record the amount of the drug absorbed by the biological unit.

The flow chart of FIG. 5 illustrates one method of quantifying the amount of $^{14}C$ derived from a biochemical sample containing $^{14}C$ and $^{12}C$ using cavity ring down spectroscopy by using a light source to direct a light beam into a sample cavity, monitoring the light beam and mode matching the light beam to the cavity, introducing the sample containing $^{14}C$ and $^{12}C$ into the cavity, using a multiplicity of mirrors to direct the light beam in the cavity to make a multiplicity of passes in the cavity and interact with the sample containing $^{14}C$ and $^{12}C$, and turning the light source off and detecting the exponentially decaying light intensity from the light beam in the cavity for measuring the amounts of $^{14}C$ and $^{12}C$ and quantifying the amount of $^{14}C$ derived from the biochemical sample. In various embodiments, the step of detecting the exponentially decaying light intensity from the light beam in the cavity for measuring the amounts of $^{14}C$ and $^{12}C$ and quantifying the amount of $^{14}C$ derived from the biochemical sample includes computing a carbon-14 concentration from a detector signal by fitting a spectroscopic model to a measured spectrogram wherein the spectroscopic model accounts for contributions from one or more interfering species that spectroscopically interfere with carbon-14.

The flow chart of FIG. 5 illustrates another method of quantifying the amount of $^{14}C$ derived from a biochemical sample containing $^{14}C$, $^{13}C$, and $^{12}C$ using cavity ring down spectroscopy by using a light source to direct a light beam into a sample cavity, monitoring the light beam and mode matching the light beam to the cavity, introducing the sample containing $^{14}C$, $^{13}C$, and $^{12}C$ into the cavity, using a multiplicity of mirrors to direct the light beam in the cavity to make a multiplicity of passes in the cavity and interact with the sample containing $^{14}C$, $^{13}C$, and $^{12}C$, and turning the light source off and detecting the exponentially decaying light intensity from the light beam in the cavity for measuring the amounts of $^{14}C$, $^{13}C$ and $^{12}C$ and quantifying the amount of $^{14}C$ derived from the biochemical sample. In various embodiment the step of detecting the exponentially decaying light intensity from the light beam in the cavity for measuring the amounts of $^{14}C$ and $^{12}C$ and quantifying the amount of $^{14}C$ derived from the biochemical sample includes computing a carbon-14 concentration from a detector signal by fitting a spectroscopic model to a measured spectrogram wherein the spectroscopic model accounts for contributions from one or more interfering species that spectroscopically interfere with carbon-14.

Optical Spectrometer Provides Analysis of Carbon-14

Figure 6:
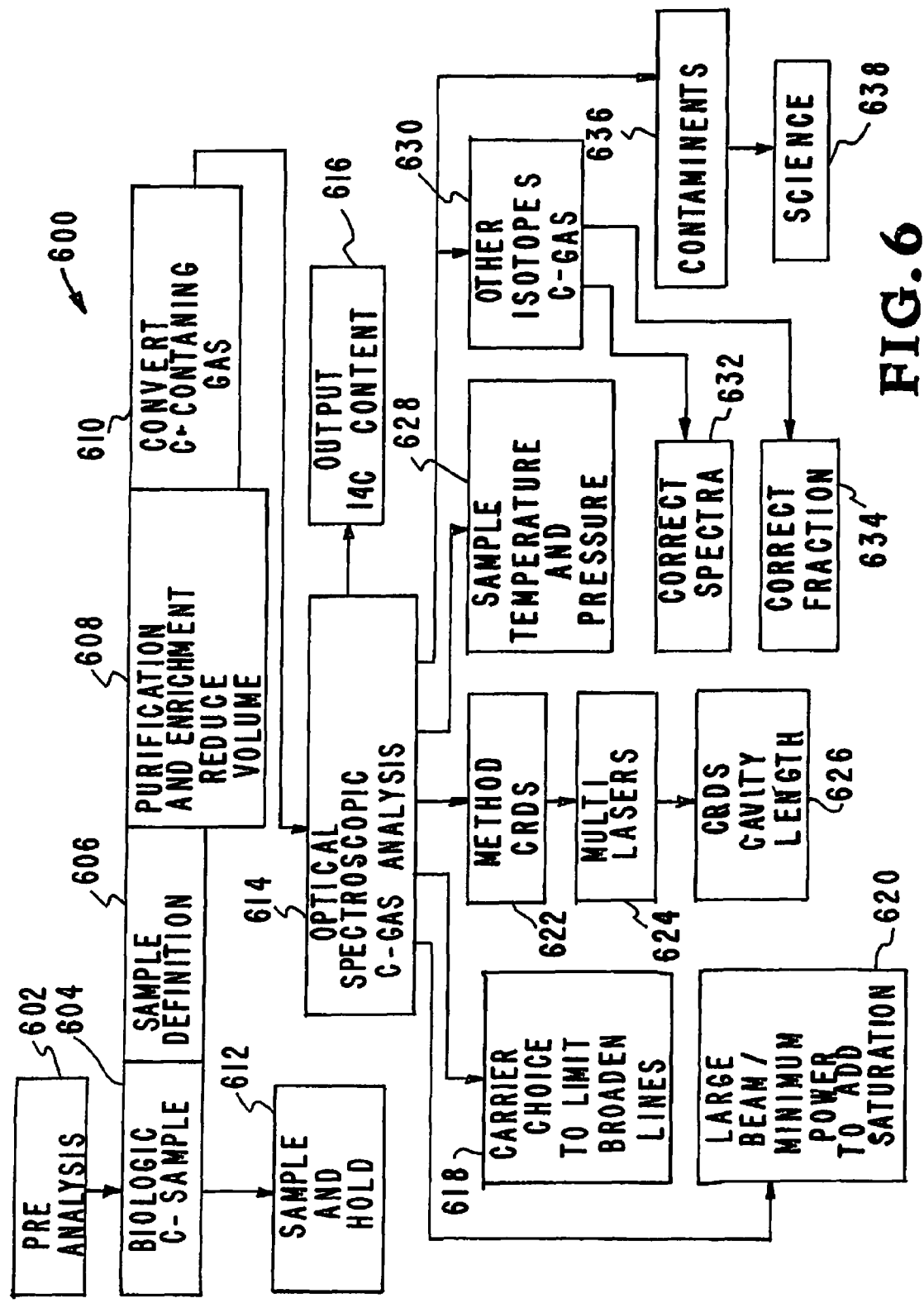
FIG. 6 is a flow chart that illustrates additional features of the disclosed apparatus, systems, and methods.

FIG. 6 a flow chart illustrates additional features of the inventor's apparatus, systems, and methods. The flow chart is designated generally by the reference numeral 600. The inventor's apparatus, systems, and methods illustrated in the flow chart 600 provide an optical spectrometer for analysis of carbon-14 including a resonant optical cavity configured to accept a sample gas including carbon-14, an optical source configured to deliver optical radiation to the resonant optical cavity, an optical detector configured to detect optical radiation emitted from the resonant cavity and to provide a detector signal; and a processor configured to compute a carbon-14 concentration from the detector signal, wherein computing the carbon-14 concentration from the detector signal includes fitting a spectroscopic model to a measured spectrogram, wherein the spectroscopic model accounts for contributions from one or more interfering species that spectroscopically interfere with carbon-14.

As illustrated in FIG. 6, the flow chart 600 shows the apparatus, systems, and methods identified and described below. It is to be understood that only some of the disclosed apparatus, systems, and methods are used in various embodiments. It is also to be understood that additional apparatus, systems, and methods can be used in various embodiments.

602—pre-analysis,
604—biological C-sample,
606—sample definition,
608—purification and enrichment and reduce volume,
610—convert C-containing gas,
612—sample and hold,
614—optical spectroscopic C-gas analysis,
616—output $^{14}C$ content,
618—carrier choice to limit broaden lines,
620—large beam/minimum power to add saturation,
622—methods CRDS,
624, multi lasers,
626 CRDS cavity length,
628—sample temperature and pressure,
630—other isotopes C-gas,
632—correct spectra, 634—correct fraction,
636—contaminants, and
638—science.

The inventor's apparatus, systems, and methods illustrated in the flow chart 600 provide background correction for the required precision to quantify the amount of $^{14}C$ derived from biochemicals using cavity ring down spectroscopy (CRDS). The inventor's apparatus, systems, and methods illustrated in the flow chart 600 provide an optical spectrometer for analysis of carbon-14 that includes a resonant optical cavity configured to accept a sample gas including carbon-14; an optical source configured to deliver optical radiation to the resonant optical cavity; an optical detector configured to detect optical radiation emitted from the resonant cavity and to provide a detector signal; and a processor configured to compute a carbon-14 concentration from the detector signal; wherein computing the carbon-14 concentration from the detector signal includes fitting a spectroscopic model to a measured spectrogram; wherein the spectroscopic model accounts for contributions from one or more interfering species that spectroscopically interfere with carbon-14.

Additional features of the inventor's apparatus, systems, and methods include the previously described optical spectrometer wherein the interfering species have greater concentration in the sample gas than the concentration of carbon-14 in the sample gas. The previously described optical spectrometer wherein the rare species has an abundance of 1000 parts per trillion or less in the gas sample, and wherein the carbon-14 concentration in the gas sample is quantified with a precision of 10% of the abundance or better. The previously described optical spectrometer wherein the optical spectrometer is further configured to reduce spectroscopic interference by operating at a sample gas temperature between about −12° C. and about 0° C. The previously described optical spectrometer wherein the optical spectrometer is further configured to reduce spectroscopic interference by operating at a sample gas pressure of about 75 Torr or less. The previously described optical spectrometer wherein the optical spectrometer is further configured to reduce spectroscopic interference by processing and/or purifying an input sample gas to deliver a processed sample gas to the resonant optical cavity. The previously described optical spectrometer wherein the processing the input sample gas comprises a method selected from the group consisting of: chromatography, passage through species selective membranes, passage through a cold trap, and combustion in a combustion reactor. The previously described optical spectrometer wherein the processing the input sample gas comprises reducing concentrations of one or more interfering species selected from the group consisting of: $N_2O$, $CO$, $CO_2$, $H_2O$, $O_3$, $CH_4$, and all stable isotopes thereof. The previously described optical spectrometer wherein the interfering species include one or more species chemically distinct from a carbon-14 containing species being measured. The previously described optical spectrometer wherein the interfering species include one or more isotopologues distinct from a carbon-14 containing isotopologue being measured.

The optical spectrometer in one embodiment includes a sample preparation unit configured to convert a biological sample to the sample gas. The previously described optical spectrometer wherein the sample preparation unit comprises a combustion chamber having carbon dioxide as the relevant species in the sample gas. The previously described optical spectrometer wherein the sample preparation unit comprises a reduction chamber having carbon monoxide as the relevant species in the sample gas. The previously described optical spectrometer wherein the sample preparation unit comprises a chemical reactor having methane as the relevant species in the sample gas. The previously described optical spectrometer wherein the optical spectrometer is further configured to compensate for spectroscopic interference by determining concentrations of one or more of the interfering species via one or more auxiliary concentration measurements and using results from the auxiliary concentration measurements when fitting the spectroscopic model. The previously described optical spectrometer wherein a time constant for an exponential decay in time is determined from the detector signal. The previously described optical spectrometer wherein the time constant is used to determine an absorbance of the sample gas. The previously described optical spectrometer wherein the detector signal is analyzed to provide separate linear absorbance and saturated absorbance terms.

One of the co-inventors of the subject application, Alan Daniel McCartt, completed a dissertation titled: "DEVELOPMENT OF A LOW-TEMPERATURE CAVITY RING-DOWN SPECTROMETER FOR THE DETECTION OF CARBON-14, A DISSERTATION SUBMITTED TO THE DEPARTMENT OF MECHANICAL ENGINEERING AND THE COMMITTEE ON GRADUATE STUDIES OF STANFORD UNIVERSITY IN PARTIAL FULFILLMENT OF THE REQUIREMENTS FOR THE DEGREE OF DOCTOR OF PHILOSOPHY." Alan Daniel McCartt's completed dissertation is summarized below.

This thesis covers the development and performance analysis of a cavity ring-down spectrometer (CRDS) prototype for the measurement of carbon-14. The overarching goal of the project was to build a prototype spectrometer using simple hardware to elucidate the hurdles in bringing a commercial carbon-14 CRDS analyzer to market. The development of the CRDS system is described. First, the theoretical analysis of the mid-IR spectra and line selection are presented. Then the hardware design choices that would enable measurements at low temperatures are discussed. Finally, the operation of the instrument is covered. This includes the experimental condition control systems and a model-based, closed-loop, PZT-creep-compensation, data-acquisition routine. Performance analysis of the spectrometer was conducted. Initial spectroscopic measurements characterized the interfering spectra surrounding the $^{14}CO2$ P(40) line candidate. This characterization was later used to quantify carbon-14 in room temperature carbon dioxide with a spectroscopic model. Finally, low-temperature trial measurements were made to elucidate any design flaws. The alpha prototype showed promise, but design flaws prevented measurements at the ideal temperature and wavelength. However, it demonstrated low-temperature measurement capabilities and resolved room temperature samples with a $^{14}C/C$ concentration approximately 50 times contemporary atmospheric levels with 6.6% 1-sigma error.

Alan Daniel McCartt is one of the co-inventors of the subject application. His dissertation was submitted to the Department of Mechanical Engineering, Stanford University in July 2014 and was accepted by the Registrar Jul. 17, 2014. His dissertation was available after Jul. 17, 2014 at Stanford Digital Repository, Collection: Electronic Theses and Dissertations. Alan Daniel McCartt's, dissertation: "DEVELOPMENT OF A LOW-TEMPERATURE CAVITY RING-DOWN SPECTROMETER FOR THE DETECTION OF CARBON-14, A DISSERTATION SUBMITTED TO THE DEPARTMENT OF MECHANICAL ENGINEERING AND THE COMMITTEE ON GRADUATE STUDIES OF STANFORD UNIVERSITY IN PARTIAL FULFILLMENT OF THE REQUIREMENTS FOR THE DEGREE OF DOCTOR OF PHILOSOPHY" is incorporated herein in its entirety for all purposes by this reference.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. An optical spectrometer for analysis of carbon-14, the optical spectrometer comprising:
   a resonant optical cavity configured to accept a sample gas including carbon-14;
   an optical source configured to deliver optical radiation to the resonant optical cavity;
   an optical detector configured to detect optical radiation emitted from the resonant cavity and to provide a detector signal; and
   a processor configured to compute a carbon-14 concentration from the detector signal;

wherein computing the carbon-14 concentration from the detector signal includes fitting a spectroscopic model to a measured spectrogram;

wherein the spectroscopic model accounts for contributions from one or more interfering species that spectroscopically interfere with carbon-14.

2. The optical spectrometer of claim 1, wherein the interfering species have greater concentration in the sample gas than the concentration of carbon-14 in the sample gas.

3. The optical spectrometer of claim 1, wherein carbon-14 has an abundance of 1000 parts per trillion or less in the sample gas, and wherein the carbon-14 concentration in the sample gas is quantified with a precision of 10% of the abundance or better.

4. The optical spectrometer of claim 1, wherein the optical spectrometer is further configured to reduce spectroscopic interference by operating at a sample gas temperature between about −12° C. and about 0° C.

5. The optical spectrometer of claim 1, wherein the optical spectrometer is further configured to reduce spectroscopic interference by operating at a sample gas pressure of about 75 Torr or less.

6. The optical spectrometer of claim 1, wherein the optical spectrometer is further configured to reduce spectroscopic interference by processing and/or purifying an input sample gas to deliver a processed sample gas to the resonant optical cavity.

7. The optical spectrometer of claim 6, wherein the processing the input sample gas comprises a method selected from the group consisting of: chromatography, passage through species selective membranes, passage through a cold trap, and combustion in a combustion reactor.

8. The optical spectrometer of claim 7, wherein the processing the input sample gas comprises reducing concentrations of one or more interfering species selected from the group consisting of: $N_2O$, $CO$, $CO_2$, $H_2O$, $O_3$, $CH_4$, and all stable isotopes thereof.

9. The optical spectrometer of claim 1, wherein the interfering species include one or more species chemically distinct from a carbon-14 containing species being measured.

10. The optical spectrometer of claim 1, wherein the interfering species include one or more isotopologues distinct from a carbon-14 containing isotopologue being measured.

11. The optical spectrometer of claim 1, further comprising a sample preparation unit configured to convert a biological sample to the sample gas.

12. The optical spectrometer of claim 11, wherein the sample preparation unit comprises a combustion chamber having carbon dioxide as the relevant species in the sample gas.

13. The optical spectrometer of claim 11, wherein the sample preparation unit comprises a reduction chamber having carbon monoxide as the relevant species in the sample gas.

14. The optical spectrometer of claim 11, wherein the sample preparation unit comprises a chemical reactor having methane as the relevant species in the sample gas.

15. The optical spectrometer of claim 1, wherein the optical spectrometer is further configured to compensate for spectroscopic interference by determining concentrations of one or more of the interfering species via one or more auxiliary concentration measurements and using results from the auxiliary concentration measurements when fitting the spectroscopic model.

16. The optical spectrometer of claim 1, wherein a time constant for an exponential decay in time is determined from the detector signal.

17. The optical spectrometer of claim 16, wherein the time constant is used to determine an absorbance of the sample gas.

18. The optical spectrometer of claim 1, wherein the detector signal is analyzed to provide separate linear absorbance and saturated absorbance terms.

* * * * *